United States Patent [19]

Lynch

[11] 4,128,397

[45] Dec. 5, 1978

[54] SULFUR DIOXIDE LIBERATION COMPOSITIONS AND METHODS OF USING SAME

[75] Inventor: David J. Lynch, Copthorne Bank, England

[73] Assignee: Rentokil Limited, East Grinstead, England

[21] Appl. No.: 627,666

[22] Filed: Oct. 31, 1975

[30] Foreign Application Priority Data

Oct. 31, 1974 [GB] United Kingdom ............... 47242/74

[51] Int. Cl.$^2$ ...................... A61L 13/00; A01N 11/00
[52] U.S. Cl. ...................................... 422/29; 424/128; 424/148; 424/162; 424/164; 424/325
[58] Field of Search ............................... 424/162, 164

[56] References Cited

U.S. PATENT DOCUMENTS

| 3,105,790 | 10/1963 | Bartholemew | 424/162 X |
|---|---|---|---|
| 3,928,577 | 12/1975 | Kochurova et al. | 424/164 |

*Primary Examiner*—Leonard Schenkman
*Attorney, Agent, or Firm*—Haight & Huard

[57] ABSTRACT

Compositions capable of giving extended release of sulphur dioxide, for use as sterilizing compositions especially in the temporary disposal of soiled sanitary and surgical dressings, comprising a sulphur-dioxide-liberation compound, for example a metabisulphite or a dithionite, and a sulfur-dioxide-liberation moderator, especially a thiosulphate and/or a phosphate.

21 Claims, No Drawings

SULFUR DIOXIDE LIBERATION COMPOSITIONS AND METHODS OF USING SAME

This invention relates to compositions capable of giving extended release of sulphur dioxide. Those compositions are particularly useful, *inter alia*, as sterilising compositions, and are especially suitable for use in the temporary disposal and storage of soiled sanitary and surgical dressings under sterile conditions prior to permanent disposal of the dressings, for example, by incineration.

Soiled dressings are an extremely efficient bacterial growth medium and various methods have been proposed for their temporary disposal. Such temporary disposal can be problematic, however, especially in such situations as public conveniences where a disposal unit for sanitary dressings may not be emptied for a period of several days or even weeks. One method for the temporary disposal of soiled dressings is to place them in a liquid disinfectant medium such as formaldehyde, but this generally involves the need for saturation of the dressings with the medium, which presents problems when the disposal unit becomes too full. Moreover, over a period of time the antibacterial or disinfectant liquid becomes weakened, and, in any case, the volume of liquid that must be present in the disposal unit limits the number of dressings that can be placed in the unit.

Sulphur dioxide has been known for many years to be a very efficient sterilising agent, both in solution and in vapour form in a moist atmosphere. The main problem associated with the use of sulphur dioxide for such purposes as the temporary disposal of soiled dressings in that its sterilising action is transitory. This is because most chemical reactions producing sulphur dioxide are fast reactions with the gaseous sulphur dioxide being evolved fairly quickly and the reaction being exhausted after a fairly short period of time. The sulphur dioxide produced gradually diffuses into the atmosphere and leaves a sulphur dioxide concentration that is insufficient to be effective.

Sulphur dioxide has been found to be an excellent sterilising medium for articles such, for example, as soiled sanitary and surgical dressings, in that it reduces bacterial growth very considerably or even eliminates it. It has the additional advantage that, because of its reducing action, it has an inhibiting effect on oxidation reactions, which frequently produce malodours. It has now been found that it is possible to produce sulphur dioxide from a composition sufficiently slowly that the composition is not rapidly exhausted but continues to liberate sulphur dioxide for a prolonged period of time.

The present invention provides a composition capable of giving extended release of sulphur dioxide in the presence of moisture, which comprises a sulphur-dioxide-liberation compound and a sulphur-dioxide-liberation moderator.

By using such a composition in a closed, but periodically opened, container such as a disposal unit for sanitary dressings, it is possible to maintain an active concentration of sulphur dioxide within the container for a period of up to several weeks.

Compounds that will liberate sulphur dioxide in the presence of water are well known. For example, metabisulphites and dithionites will decompose in the presence of water with the liberation of sulphur dioxide, and these compounds have been found to be particularly suitable for use as sulphur-dioxide-liberating compounds in the compositions according to the invention. They are conveniently used in the form of the respective sodium salts ($Na_2S_2O_5$ and $Na_2S_2O_4$ respectively) since these are readily obtainable.

Various sulphur-dioxide-liberation moderators can be used in the compositions according to the invention, and the particular moderator chosen in any given case will depend partly on the sulphur-dioxide-liberation compound used and also on the intended use of the particular composition. In general terms, the effect of the moderator is to decrease the rate at which the sulphur dioxide is liberated from the sulphur-dioxide-liberating compound, as compared with the rate at which it is liberated in the absence of the moderator. That is not to say that the presence of the moderator results in the liberation of substantially less sulphur dioxide, but that it results in the liberation of a substantially similar amount of sulphur dioxide, as compared with the amount liberated in the absence of the moderator, at a lower rate and thus over an extended period of time. Thus, the composition is described as being "capable of giving extended release of sulphur dioxide".

While all the moderators have the above-described general effect, this can be manifested in different ways by different moderators. Certain moderators, for example, will result in the liberation of sulphur dioxide from the composition at a substantially constant rate over a period of several days or even weeks, and this can be particularly advantageous for use in such situations as disposal units for sanitary dressings in public conveniences as described above. Other moderators will result in the liberation of sulphur dioxide at a gradually decreasing rate, and this can be useful in situations where it is desired to establish fairly rapidly an active concentration of sulphur dioxide and then to maintain an active concentration over a period of time by the continued liberation of sulphur dioxide at a decreased rate to compensate for leakage of the sulphur dioxide. Still other moderators will result in the liberation of sulphur dioxide at an initially increasing rate and then at a decreasing rate, and this can be useful where it is desired to effect a gradual build-up of the concentration of sulphur dioxide and then to maintain an active concentration. In all cases, however, the sulphur dioxide is liberated over a period of time greater than that over which it would be liberated in the absence of a moderator.

The action of a particular moderator, and thus its suitability for a particular purpose, may be ascertained by means of simple preliminary tests, such as those described below in Example 1.

The manner in which the moderator functions to cause the slower liberation of the sulphur dioxide is not clear or certain, but again appears to vary according to the particular moderator used. Certain moderators, for example, are simply buffers and appear to function by maintaining the pH of an aqueous solution of the composition at a value such that sulphur dioxide is liberated at a decreased rate. The manner in which other moderators function appears to be somewhat more complicated: it is thought that some moderators function by taking up a certain proportion of the sulphur dioxide given off by the sulphur-dioxide-liberation compound and returning this proportion to the sulphur-dioxide-liberation compound, so that only a certain amount of free sulphur dioxide is liberated in each cycle of reactions.

(It is to be emphasised, however, that the present invention is not restricted to any particular mode of action of the moderator or to any particular chemical theory as to the manner in which the moderator functions.) For certain applications, it can be advantageous to use a combination of two moderators, one of which functions in one manner and the other of which functions in another manner.

Thiosulphates have been found to be particularly effective as moderators in the compositions of the invention, the sodium salt ($Na_2S_2O_3$) generally being used since it is readily available. A thiosulphate may be used as the sole moderator in the composition, but in many cases it is advantageous to use a thiosulphate in conjunction with a second moderator that is a buffer.

Certain phosphates have also proved to be particularly effective as moderators, both as the sole moderator and, especially, in conjunction with a thiosulphate. Orthophosphates are especially to be mentioned in this respect, for example potassium dihydrogen orthophosphate ($KH_2PO_4$). Examples of other buffers that have proved suitable for use as moderators are borates, for example, a boric acid-borate mixture or borax, and amines, for example, triethylamine.

In the case of moderators that serve as buffers, the pH at which an aqueous solution of the composition is buffered depends both on the particular sulphur-dioxide-liberation compound being used and on the desired rate of liberation of sulphur dioxide, as well as on the chosen moderator. The optimum pH for a particular use may be determined by means of simple preliminary tests as mentioned above.

The relative proportions of sulphur-dioxide-liberation compound and moderator in the compositions according to the invention may vary within wide limits: in some cases, the sulphur-dioxide-liberation compound may be present in the greater amount while in other cases the moderator may be present in the greater amount. Again, the proportions chosen depend on the intended use of the composition but may be determined by simple tests.

An especially preferred composition according to the invention is one that comprises a metabisulphite as the sulphur-dioxide-liberation compound and comprises both a thiosulphate and a phosphate as moderators. Examples of other compositions according to the invention comprising a metabisulphite as the sulphur-dioxide-liberation compound are those comprising, as the moderator, a thiosulphate or a phosphate. Examples of compositions comprising a dithionite as the sulphur-dioxide-liberation compound are those comprising, as the moderator, a thiosulphate, an amine, or a borate.

The present invention also provides a method for sterilising an article, especially a soiled sanitary dressing or a soiled surgical dressing, which comprises bringing the article into contact with or into the proximity of a composition according to the invention in the presence of moisture.

The article may, for example, be brought into contact with or into the proximity of an aqueous solution of the composition. Alternatively, a moist article may be brought into contact with the dry composition, thus causing the moisture to dissolve a part of the composition and resulting in liberation of sulphur dioxide. A further alternative is for the article (whether moist or dry) to be brought into contact with or into the proximity of the dry composition in a moist atmosphere.

The term "sterilise" as used herein means to cause a substantial reduction in the number of micro-organisms but is not intended to imply that complete sterility is imparted to the article in the sense that *all* micro-organisms are completely destroyed.

By bringing the article into the proximity of the composition or solution thereof, is meant that the article may not be brought into actual contact with the composition or solution but is brought sufficiently near thereto to be sterilised by sulphur dioxide being liberated from the composition. It follows that the article must be brought into the region in which there is an active concentration of sulphur dioxide. The article may, for example, be put into the upper region of a disposal unit for sanitary dressings or other vessel containing a small amount of an aqueous solution of a composition according to the invention.

In order for the sulphur dioxide to impart sterility to an article, the concentration of sulphur dioxide in the region of the article should generally be at least 10 p.p.m. (parts per million), although the concentration required in any particular situation will depend on the ambient temperature. The term "active concentration" simply means a concentration sufficient to impart sterility to the article. Advantageously, the concentration of sulphur dioxide in the region of the article should be within the range of from 75 to 200 p.p.m.

The method of the invention is advantageously carried out in a closed container as this hinders or prevents the diffusion of the sulphur dioxide into the atmosphere and thus more readily enables an active concentration of sulphur dioxide to be maintained. It also has the advantage that the operator or user is not subjected to the unpleasantness of the presence of sulphur dioxide or at least that such unpleasantness is minimised.

The compositions and method of the invention are particularly suitable for use in closed containers of the so-called "trap-top" type, that is to say containers having a pivoted top which when opened presents a shelf on which the article to be placed in the container can be placed while keeping the container sealed and which allows the article to drop into the container when the lid is closed. Such containers remain sealed at all times, and thus leakage of sulphur dioxide is reduced to a minimum. Containers of this type are particularly suitable for use as disposal units for soiled sanitary and surgical dressings. They can be charged with a small quantity of an aqueous solution of a composition according to the invention and can then be put into use for up to several weeks, for example 3 to 4 weeks, during which time soiled dressings may be placed in the container as required. When full, or after a set interval of time, the container can be replaced by a freshly-charged container and then be taken to a disposal site where it can be emptied and the contents destroyed, for example by incineration.

It is possible, using the compositions according to the invention, to maintain a sulphur dioxide concentration of from 75 to 200 p.p.m. within such containers for a period of 3 to 4 weeks and in some cases for 6 or more weeks. A concentration of this magnitude is generally sufficient to maintain all soiled dressings or other articles within the container in a sterile state until their permanent disposal. This has been found to be the optimum sulphur dioxide concentration range, although concentrations outside this range may be used in certain cases. The concentration should not, however, generally be less than 10 p.p.m., since there is then a danger of it being ineffective, or more than 500 p.p.m., since there is then a danger of unpleasantness to persons in the vicinity of the container.

If desired, small amounts of perfume can be included in the compositions in order to mask any sulphur dioxide odour. Various other auxiliaries can also be added to the compositions, for example, auxiliaries to improve the free-flowing properties of dry compositions. This can be particularly useful when the composition is intended to be put into sackets for distribution or sale. In other cases, it can be advantageous to omit such an auxiliary since compositions that are not completely free-flowing may have the advantage of lower dust production.

Further details of the invention will be apparent from the following examples which illustrate the effectiveness of various compositions.

EXAMPLE I

Various tests were carried out to demonstrate the extended release of sulphur dioxide over a prolonged period of time using compositions according to the invention, and to compare them with the release of sulphur dioxide from sulphur-dioxide-liberation compounds in the absence of a moderator.

The sulphur-dioxide-liberation compound was dissolved in 100 ml of water or in 100 ml of a 0.1 M aqueous solution of the moderator, as appropriate, in a 500 ml vessel fitted with a perforated top and maintained at about 18° C., to give solutions of the concentrations indicated in the table below (as percentage concentration weight: volume). The initial pH of the solution was measured and then the sulphur dioxide concentration was measured within the vessel by means of Draeger tubes after set intervals ranging from ¼ hour to 12 days. (The perforated top prevented complete accumulation of sulphur dioxide, which would not give useful results for the present purposes; the leakage of sulphur dioxide through the perforated top was greater than the leakage that there would be from a "trap-top" disposal unit). The results of these tests are summarised in the table below.

for the whole period of the test, and in that the sulphur dioxide concentration was still above 10 ppm after 3 weeks. In tests 5, 6 and 7, the sulphur dioxide concentration was maintained at an active level throughout the test, whereas sulphur dioxide production from the sodium dithionite alone (test 4) had ceased after 5 days.

EXAMPLE 2

A mixture of 50.0 g of sodium metabisulphite, 8.5 g of sodium thiosulphate (anhydrous), and 13.0 g of potassium dihydrogen orthophosphate was dissolved in 1 litre of water in the bottom of a 30-litre "trap-top" sanitary-towel disposal unit. Several units containing such a mixture were then put into continuous use for a period of 4 weeks. After this time the sulphur dioxide concentration in the units was in general between 50 and 100 ppm, although in some cases it was even higher (which could be a result of different temperatures or of the addition of mildly acid towels). Sample used sanitary towels were taken from those that had been collected within the units (taken from the top, middle, and bottom of the unit) and all were found to be completely sterile, that is they gave a zero bacteria count.

This experiment demonstrates both the effectiveness of the composition in producing sulphur dioxide sufficiently slowly to maintain an active concentration thereof within the unit for several weeks, and also the effectiveness of the sulphur dioxide in maintaining sterility of the used towels.

The composition used in this example was the same as that used in test 2 of Example I, and thus the sulphur dioxide concentrations obtained in test 2 under the test conditions correspond to a sulphur dioxide concentration of from 50 to 100 ppm under use conditions in "trap-top" disposal units. Similar sulphur dioxide concentrations would, therefore, be obtained under use conditions with the compositions of tests 3, 5, 6 and 7 of Example I, since the concentrations obtained under the test conditions are similar to those in test 2.

EXAMPLE 3

Various tests were carried out in 30-litre "trap-top"

| Test | SO$_2$-liberating compound Type | Conc. | Moderator | pH of final solution | SO$_2$ concentration (p.p.m.) ¼h | 1½h | 18h | 7d | 12d |
|---|---|---|---|---|---|---|---|---|---|
| 1 | sodium metabisulphite | 5 | none | 4.3 | 50 | 70 | 140 | 48 | 9 |
| 2 | sodium metabisulphite | 5 | thiosulphate/phosphate | 4.7 | 16 | 18 | 18 | 18 | 16 |
| 3 | sodium metabisulphite | 5 | thiosulphate (5% wt/vol.) | 4.4 | 10 | 28 | 40 | 6 | 5 |
| 4 | sodium dithionite | 5 | none | 6.0 | 180 | — | 200 | 0 | 0 |
| 5 | sodium dithionite | 5 | triethylamine (pH 11.4) | 10.4 | 120 | — | 110 | 20 | 14 |
| 6 | sodium dithionite | 5 | boric acid-borate (pH 9.2) | 7.2 | 140 | — | — | 20 | 12 |
| 7 | sodium dithionite | 2.5 | boric acid-borate (pH 9.2) | 8.4 | 52 | — | 56 | 15 | 10 |
| 8 | none | — | thiosulphate (5% wt/vol.) | 5.3 | No SO$_2$ liberated | | | | |

From the results given in the table it can be seen that the presence of the moderator in the compositions according to the invention (tests 2, 3, 5, 6 and 7) gives extended release of sulphur dioxide, as compared with the release of sulphur dioxide from the sulphur-dioxide-liberation compounds without a moderator (tests 1 and 4), thus enabling an active concentration of sulphur dioxide to be maintained above the solution for an extended period of time. Test 8 simply shows that sodium thiosulphate does not act as a sulphur-dioxide-liberation compound. Test 2 is particularly notable in that the rate of sulphur dioxide liberation was such that a practically constant sulphur dioxide concentration was maintained sanitary-towel disposal units to demonstrate the extended release of sulphur dioxide over a prolonged period of time using compositions according to the invention and to compare them with the release of sulphur dioxide from sulphur-dioxide-liberation compounds in the absence of a moderator.

The sulphur-dioxide-liberation compound was dissolved in 1 litre of an aqueous solution of the moderator (or in 1 litre of water when no moderator was used) in the bottom of the disposal unit. The particular compounds and amounts used are indicated in the table below. Each unit was maintained at room temperature (about 18° C.) and the sulphur dioxide concentration in the upper region of the vessel was measured by means of Draeger tubes after set intervals ranging from 4 hours to 35 days. The results of these tests are summarised in the table below.

Tests 2 to 6 show the extended release of sulphur dioxide from various compositions comprising sodium metabisulphite and a moderator as compared with that from sodium metabisulphite alone (test 1). Test 7 uses the same amount of sodium thiosulphate as test 3 and shows that, although in certain circumstances a little sulphur dioxide may be released from sodium thiosulphate, the amount released is very small and that therefore sodium thiosulphate cannot properly be considered to be a sulphur-dioxide-liberation compound. Tests 9 and 10 show the extended release of sulphur dioxide from compositions according to the invention containing sodium dithionite as the sulphur-dioxide-liberation compound as compared with that from sodium dithionite alone (test 8).

| Test | SO$_2$ - liberating compound | | Moderator | |
|---|---|---|---|---|
| 1 | Sodium metabisulphite | 50 g | none | |
| 2 | Sodium metabisulphite | 50 g | Sodium thiosulphate | 20 g |
| 3 | Sodium metabisulphite | 20 g | Sodium thiosulphate | 50 g |
| 4 | Sodium metabisulphite | 50 g | Sodium thiosulphate | 8.5 g |
|   |   |   | Potassium dihydrogen orthophosphate | 13 g |
| 5 | Sodium metabisulphite | 50 g | Sodium acetate buffer | pH 5 |
| 6 | Sodium metabisulphite | 50 g | Potassium dihydrogen orthophosphate | 25 g |
| 7 | Sodium thiosulphate | 50 g | Citrate/phosphate buffer | pH 2.6 |
| 8 | Sodium dithionite | 50 g | none | |
| 9 | Sodium dithionite | 50 g | Triethylamine | 0.05 M |
| 10 | Sodium dithionite | 50 g | Sodium thiosulphate | 25 g |

| | SO$_2$ - concentration (p.p.m.) | | | | | | | | | | | | | | | | |
|---|---|---|---|---|---|---|---|---|---|---|---|---|---|---|---|---|---|
| Test | 4h | 24h | 2d | 5d | 9d | 11d | 13d | 14d | 15d | 16d | 20d | 21d | 27d | 28d | 31d | 32d | 35d |
| 1 | 1400 | 2000 | 2200 | 1150 | 675 | — | 200 | 80 | 0 | — | — | — | — | — | — | — | — |
| 2 | 130 | 185 | — | 113 | — | 85 | — | — | 100 | — | 110 | — | 85 | — | — | 60 | 50 |
| 3 | 95 | 50 | 55 | 35 | 60 | — | 60 | 65 | — | 70 | 70 | — | 110 | — | 105 | — | 120 |
| 4 | 165 | 200 | 190 | 125 | 130 | — | 115 | 107 | — | 110 | 110 | — | 110 | — | 120 | — | 115 |
| 5 | 300 | 1400 | 2200 | 1200 | 1200 | — | 225 | 110 | — | 20 | 0 | — | — | — | — | — | — |
| 6 | 400 | 750 | — | 400 | — | 270 | — | — | 300 | — | 350 | — | 185 | — | — | 160 | 155 |
| 7 | 110 | 50 | 40 | 2 | 0 | — | — | — | — | — | — | — | — | — | — | — | — |
| 8 | 5000 | — | — | 100 | 80 | — | — | 50 | — | 80 | — | 85 | — | 70 | — | — | 60 |
| 9 | 800 | 300 | 220 | 60 | 70 | — | — | 70 | — | 60 | — | 50 | — | 60 | 60 | — | 60 |
| 10 | 1000 | 1000 | 500 | 300 | 130 | — | — | 130 | — | 130 | — | — | — | — | — | — | 100 |

I claim:
1. A sterilizing composition capable fof giving extended release of sulphur dioxide in the presence of moisture, consisting essentially of:
   (a) a compound that will liberate sulphur dioxide in contact with water; and
   a water-soluble thiosulphate which acts as a moderator for the release of said sulphur dioxide said components a and b being present in amounts such that it is possible to produce sulphur dioxide from the composition sufficiently slowly that the composition is not rapidly exhausted but continues to liberate sulphur dioxide for a prolonged period of time.
2. A composition as claimed in claim 1, wherein the sulphur dioxide-liberating compound is a metabisulphite or a dithionite.
3. A composition as claimed in claim 2, wherein the sulphur dioxide-liberating compound is a metabisulphite, said composition further comprising, as an additional moderator for the release of sulphur dioxide, a water soluble phosphate buffer.
4. A composition as claimed in claim 2, wherein the sulphur dioxide-liberating compound is a dithionite, said composition further comprising, as an additional moderator for the release of sulphur dioxide, an amine or a borate buffer.
5. A composition as claimed in claim 3, wherein the metabisulphite is sodium metabisulphite.
6. A composition as claimed in claim 2, wherein the dithionite is sodium dithionite.
7. A composition as claimed in claim 1, wherein the thiosulphate is sodium thiosulphate.
8. A composition as claimed in claim 2, wherein the phosphate is an orthophosphate.
9. A composition as claimed in claim 4, wherein the borate is present as borax or a boric acid-borate mixture.
10. A composition as claimed in claim 4, wherein the amine is present as triethylamine.
11. A composition as claimed in claim 1, additionally comprising a perfume.
12. A composition as claimed in claim 1, additionally comprising an auxiliary to improve its free-flowing properties.
13. A composition as claimed in claim 1, in the form of an aqeous solution.
14. A method of sterilizing an article, which comprises bringing the article into contact with or into the proximity of a composition as claimed in claim 1 in the presence of moisture.
15. A method as claimed in claim 14, wherein the article is brought into contact with or into the proximity of the composition by being placed into a closed container containing a aqueous solution of the composition.
16. A method as claimed in claim 15, wherein the container is a "trap-top" container having a pivoted top which when opened presents a shelf on which the article to be placed in the container can be placed while keeping the container sealed and which allows the article to drop into the container when the lid is closed.
17. A method as claimed in claim 14 wherein the article is a soiled sanitry or surgical dressing.
18. A method as claimed in claim 14 wherein the article is brought into a region in the proximity of the composition in which the concentration of sulphur dioxide liberated from the composition is at least 10 p.p.m.

19. A method as claimed in claim 18, wherein said concentration is not more than 500 p.p.m.

20. A method as claimed in claim 18, wherein said concentration is within the range of from 75 to 200 p.p.m.

21. A method as claimed in claim 15, wherein the article is a soiled sanitary or surgical dressing which is brought into a region in the proximity of the composition in which the contraction of sulphur dioxide liberated from the composition is at least 10 p.p.m.

* * * * *

UNITED STATES PATENT AND TRADEMARK OFFICE
CERTIFICATE OF CORRECTION

PATENT NO. : 4,128,397
DATED : December 5, 1978
INVENTOR(S) : David J. Lynch

It is certified that error appears in the above-identified patent and that said Letters Patent are hereby corrected as shown below:

Claim 1, line 1: "fof" should be ----of---- line 6: insert ----(b)---- at beginning of line

Signed and Sealed this

Twenty-sixth Day of February 1980

[SEAL]

Attest:

SIDNEY A. DIAMOND

Attesting Officer     Commissioner of Patents and Trademarks